United States Patent [19]

Squire

[11] 4,261,901
[45] Apr. 14, 1981

[54] SYNTHESIS OF TETRAHYDROFURAN
[75] Inventor: Edward N. Squire, Glen Mills, Pa.
[73] Assignee: E. I. Du Pont de Nemours and Company, Wilmington, Del.
[21] Appl. No.: 74,097
[22] Filed: Sep. 10, 1979
[51] Int. Cl.$^3$ ........................................... C07D 307/08
[52] U.S. Cl. ........................... 260/346.11; 260/347.91; 568/848; 568/879
[58] Field of Search ...................... 260/346.11, 347.91; 568/848, 879

[56] References Cited

U.S. PATENT DOCUMENTS

| | | | |
|---|---|---|---|
| 2,335,027 | 11/1943 | Ritter | 568/879 |
| 3,290,395 | 12/1966 | Bohm et al. | 568/848 |
| 3,414,588 | 12/1968 | Jones | 260/346.11 X |
| 3,438,997 | 4/1969 | Fetterly et al. | 260/340.7 |
| 3,527,770 | 9/1970 | Stapp | 260/345.1 |
| 3,527,771 | 9/1970 | Stapp | 260/345.1 |
| 3,574,773 | 4/1971 | Mueller et al. | 260/638 |
| 3,644,427 | 2/1972 | Stapp | 260/345.1 |
| 3,818,043 | 6/1974 | Starks | 260/340.7 |
| 3,954,842 | 5/1976 | Stapp | 260/476 R |
| 3,956,407 | 5/1976 | Stapp | 260/638 R |
| 3,956,408 | 5/1976 | Stapp | 260/638 R |
| 3,960,972 | 6/1976 | Stapp | 260/638 R |
| 3,960,973 | 6/1976 | Stapp | 260/638 R |
| 3,993,702 | 11/1976 | Hawkins | 260/632 B |
| 4,002,646 | 1/1977 | Robinson | 260/346.11 |
| 4,005,112 | 1/1977 | Smith | 260/346.11 |
| 4,005,113 | 1/1977 | Smith | 260/346.11 |
| 4,010,171 | 3/1977 | Smith | 260/346.11 |
| 4,011,244 | 3/1977 | Smith | 260/346.11 |
| 4,081,486 | 3/1978 | Stapp | 260/638 R |

FOREIGN PATENT DOCUMENTS

| | | |
|---|---|---|
| 851755 | 9/1970 | Canada . |
| 696725 | 9/1940 | Fed. Rep. of Germany . |
| 1279014 | 10/1968 | Fed. Rep. of Germany . |
| 1216271 | 12/1970 | United Kingdom . |
| 1228991 | 4/1971 | United Kingdom . |

Primary Examiner—Richard Raymond

[57] ABSTRACT

Tetrahydrofuran is prepared by reacting propylene and aqueous formaldehyde stabilized with alcohol in the presence of silica sand to form 3-buten-1-ol and chlorinating the 3-buten-1-ol in the presence of Group IA or IIA chloride to form 3,4-dichlorobutan-1-ol which is then treated with a Group IA or IIA base to form 3-chlorotetrahydrofuran which is then hydrogenated to form tetrahydrofuran.

5 Claims, No Drawings

SYNTHESIS OF TETRAHYDROFURAN

BACKGROUND OF THE INVENTION

1. Field of the Invention

This invention relates to a four-step process for the production of tetrahydrofuran in improved yield comprising the reaction of propylene with formaldehyde in the presence of silica sand followed by chlorination, cyclization and hydrogenation of the respective intermediates.

2. Description of the Prior Art

The reaction of olefins with aldehydes is known in the art. The "Prins-Reaction", for example, relates to a reaction between an olefin and an aldehyde in the presence of a strong acid. Many variations of this reaction have been advanced to improve the yield of desired products or to alter the reaction to produce more useful products.

U.S. Pat. No. 2,335,027 describes such a reaction in the absence of a catalyst and U.S. Pat. No. 3,574,773 calls for the presence of a base.

U.S. Pat. No. 3,290,395 discloses the chlorination of unsaturated alcohols in the absence of water and in the presence of hydrogen chloride.

Cyclization of chlorobutanols to tetrahydrofuran is known in the prior art. The usual procedure is to treat the chlorobutanol with aqueous or alcoholic base.

German No. 696,725 discloses a process for 3-chlorotetrahydrofuran whereby a vinyl ether alcohol is treated with chlorine and the 3,4-dichlorobutanol formed is subjected to an HCl-split treatment with sodium hydroxide.

U.S. Pat. No. 3,527,770 relates to the reductive dehalogenation of 4-halotetrahydropyrans to tetrahydropyrans by contact with a Group VIII metal compound and hydrogen.

SUMMARY OF THE INVENTION

The process of the present invention is directed to the preparation of tetrahydrofuran from propylene and formaldehyde in a process comprising (1) reacting propylene and aqueous formaldehyde stabilized with alcohol in the presence of silica sand at a temperature of from 250°–350° C. and a pressure of from 50–800 atmospheres in the absence of oxygen at a ratio of propylene to formaldehyde of at least 1:1 to form 3-buten-1-ol;

(2) reacting the aqueous 3-buten-1-ol with chlorine in the presence of Group IA or IIA chloride at a temperature of from 0°–50° C. and a pressure of from 5 to 50 psia in the absence of oxygen to form 3,4-dichlorobutan-1-ol;

(3) treating 3,4-dichlorobutan-1-ol with an aqueous or alcoholic solution of a Group IA or IIA base at a temperature of from 25°–200° C. and a pressure of from atmospheric to 50 psia in the absence of oxygen to form 3-chlorotetrahydrofuran or a mixture of 3-chlorotetrahydrofuran with 2,3-dihydrofuran and or 2,5-dihydrofuran;

(4) hydrogenating 3-chlorotetrahydrofuran and/or the byproduct 2,3-dihydrofuran and 2,5-dihydrofuran in an aqueous medium with hydrogen and in the presence of a hydrogenation catalyst at a temperature of from 50°–250° C. and a pressure of 147–2000 psia in the absence of oxygen to form tetrahydrofuran.

Tetrahydrofuran is an important product of commerce. Its principle utility is as an intermediate for the manufacture of polymers such as elastomers, plastics, fibers and most importantly as a solvent. Commercially, tetrahydrofuran is usually made by one of three routes based on the starting materials: acetylene/formaldehyde; furfural; and butadiene/chlorine. Although all three of the above processes are used, there is a need brought about by commercial demand and energy factors to produce tetrahydrofuran in high yields and from less expensive starting materials.

DETAILED DESCRIPTION OF THE INVENTION

3-Buten-1-ol Synthesis

3-Buten-1-ol is prepared by reacting propylene and aqueous formaldehyde stabilized with alcohol in the presence of silica sand at a temperature of from 250°–350° C. and a pressure of from 50–800 atmospheres in the absence of oxygen at a propylene to formaldehyde ratio of at least 1:1.

The aqueous formaldehyde is preferably 37% by weight formaldehyde in water. However, more dilute formaldehyde may be used. The aqueous formaldehyde is stabilized with an alcohol, e.g., methyl alcohol. Generally, the amount of methyl alcohol used to stabilize 37% formaldehyde is 12–15% by weight based on the aqueous formaldehyde. The ratio of propylene to formaldehyde can generally be at least 1:1, preferably 1:1–2:1. However, there is no advantage in using ratios of greater than 2:1. Ratios of less than 1:1 are not used because the excess formaldehyde will result in polymerization of the formaldehyde and side products.

The reaction temperature for the propyleneformaldehyde reaction can generally be from 250°–350° C., preferably from 280°–330° C.

In all four of the process steps for the synthesis of tetrahydrofuran, oxygen should be eliminated from the presence of the reactants. Aldehydes, unsaturated compounds and tetrahydrofuran will all react with oxygen. Nitrogen, helium and argon are examples of gases which may be used; however, if the reactor and lines were purged with a reactant or filled with water vapor, for example, so that air is excluded, the same purpose would be achieved.

The catalyst for the propylene-formaldehyde reaction is silica sand. The silica sand is available from the Fisher Scientific Co. in the form of a fine granular dust. The amount of silica sand is not critical. However, generally a mole amount equal to the moles of propylene in the reaction is used.

The 3-buten-1-ol that is formed is useful as a monomer in polymerization reactor. It has now been found that it is also useful as an intermediate for the preparation of tetrahydrofuran.

3,4-Dichlorobutan-1-ol Synthesis

When used as an intermediate in the synthesis of tetrahydrofuran, aqueous 3-buten-1-ol is reacted with chlorine in the presence of a Group IA or IIA chloride at a temperature of from 0°–50° C. and a pressure of from 5–50 psia in the absence of oxygen and 3,4-dichlorobutan-1-ol is formed.

A high chloride ion concentration in the mixture and low temperatures are preferred to minimize side reactions due to hydroxyl group involvement. An amount of calcium chloride or sodium chloride sufficient to form a saturated solution is most preferred.

The temperature can range from 0°–50° C., preferably 1°–40° C. and most preferably 0°–18° C. At atmospheric pressures and temperatures below 0° C. the reaction is slow and at temperatures above 50° C. the amount of side products increases.

Furan Ring Synthesis

The 3,4-dichlorobutan-1-ol is then reacted with an aqueous or alcoholic solution of a Group IA or IIA base, e.g., sodium hydroxide and calcium hydroxide at a temperature of from 25°–200° C. and a pressure of from atmospheric to 50 psia with absence of oxygen to form 3-chlorotetrahydrofuran or a mixture of 3-chlorotetrahydrofuran with 2,3-dihydrofuran and or 2,5-dihydrofuran.

It is preferable to add the base during the course of the reaction in a sufficient amount at such a rate that the pH remains in the range of about 6–8. The amount of the base can range from one to two equivalents per mole of 3,4-dichlorobutan-1-ol; preferably about 1.1 equivalents per mole are used. Treatment of 3,4-dichlorobutan-1-ol with excess base produces some 2,3- and 2,5-dihydrofurans. These compounds can also be hydrogenated to tetrahydrofuran in the next step of this process.

Representative examples of the Group IA and IIA bases include sodium hydroxide, potassium hydroxide, calcium hydroxide, calcium carbonate, calcium oxide, potassium bicarbonate, potassium carbonate and mixtures thereof. The preferred bases are sodium hydroxide and calcium hydroxide.

An example of a suitable alcohol is n-butanol. The temperature of the 3,4-dichlorobutan-1-ol reaction can be from room temperature to 200° C., preferably from 100°–140° C. Temperatures above 200° C. will lead to more side products. Temperatures below room temperature are not desired because the reaction rate is so slow.

Tetrahydrofuran Synthesis

When 3-chlorotetrahydrofuran or the by-products 2,3- and 2,5-dihydrofuran in an aqueous medium are treated with hydrogen in the presence of a hydrogenation catalyst at a temperature of 50°–250° C. and a pressure of 147–2000 psia, in the absence of oxygen, tetrahydrofuran is formed. The addition of a base such as calcium carbonate or calcium oxide to the medium is preferred in order to neutralize the hydrogen chloride which is formed in the reaction.

The catalyst for the hydrogenation may be palladium, rhodium, ruthenium or nickel. Generally, a catalytic amount of the catalyst is operable. Preferably 0.1–10% by weight of the catalyst based on the 3-chlorotetrahydrofuran is used. A 10% palladium on charcoal catalyst or a 10% rhodium on carbon catalyst is preferred. Both of these catalysts were found superior at 120° C. to ruthenium on alumina and nickel on Kieselguhr catalyst.

The temperature for the hydrogenation can be from 50°–250° C., preferably 80°–150° C. Lower temperatures result in a slower reaction. Higher temperatures are not desired because of increased corrosion.

The process of the present invention is further illustrated by the examples that follow wherein all percentages and parts are by weight unless otherwise indicated. Yields and conversions are on a mole basis.

EXAMPLE 1

3-Buten-1-ol Synthesis (Best Mode)

A 180 ml mild steel shaker tube is charged with 48 g 37% aqueous formaldehyde containing 12–15% methyl alcohol (0.59 mole $CH_2O$) and 60 g silica sand (Fisher Scientific Co.). The tube is closed and chilled to $-80°$ C. and alternatively evacuated and flushed three times with nitrogen. The evacuated tube is then charged with 42 g propylene, closed, and agitated on a pendulum shaker heated to 300° C. at 400 atmospheres and held at this temperature for 10 minutes (84–0.305 m strokes/minute). The tube is cooled, chilled, and the propylene gas slowly vented. After opening the tube and separating the liquid from the sand the liquid is analyzed by gas chromatography on two columns, a 1.83 m$\times 0.635 \times 10^{-2}$ m diameter Porapak R and a 1.83 m$\times 0.635 \times 10^{-2}$ m diameter Carbowax ® 20 M. The conversion of formaldehyde to 3-buten-1-ol is found to be 27%; the absolute yield 70% and the yield including the recyclable 4-methyl-1,3-dioxane and 1,3-butandiol is 88% based on the formaldehyde.

Other catalysts were explored in an effort to attain the best yield of 3-buten-1-ol from the reaction of aqueous formaldehyde with propylene. These catalysts included strong and weak protonic acids such as HCl, $H_2SO_4$, acetic acid, and boric acid. Also studied were such nonprotonic acids as $WO_3$, silica gels, germanium dioxide, and aluminas. None of these could compare in yield to the silica sand. This was largely due to side reactions which occur in the presence of these other catalysts.

EXAMPLE 2

3,4-Dichlorobutan-1-ol Synthesis (Best Mode)

A 300 ml, 3-neck, round bottom, glass flask equipped with a chlorine inlet tube, dry ice condenser, thermometer and magnetic stirrer was charged with 2.2 g $CaCl_2$, 3.6 g distilled water and 7.2 g 3-buten-1-ol under 1 atm $N_2$. The mixture was vigorously stirred, chilled to 10° C. by immersion of the flask in ice and chlorine gas introduced above the liquid at an average rate approximately 4 g/hr. At the end of two hours, the temperature had dropped to 5° C. and the chlorine flow was stopped.

The flask was rinsed out with ether and water, and the water solution extracted with ether. Analysis of the ether solution by gas chromatography on a 1.83 m$\times 0.635 \times 10^{-2}$ m diameter 3% OV 17 column showed a $ClCH_2CHClCH_2CH_2OH$ yield of 91.5% at 100% conversion of the 3-buten-1-ol.

In a similar experiment using the same quantities of starting materials except omitting the water and introducing the chlorine in 1¼ hours at 7°–12° C., the yield of $ClCH_2CHClCH_2CH_2OH$ was 93.6% at 100% conversion of the 3-buten-1-ol.

The $ClCH_2CHClCH_2CH_2OH$ was characterized by NMR, IR and mass spectra.

The major byproduct,

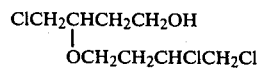

(3A, 4-chlorobutan-1-ol) was also characterized by IR, mass spectra and its subsequent conversion to the corresponding 3-alkoxytetrahydrofuran.

Confirmatory evidence for the origin of the 3A, 4-chlorobutan-1-ol was provided by the syntheses of 3-methoxy-4-chlorobutan-1-ol and 3-isobutoxy-4-chlorobutan-1-ol.

In five experiments similar to Example 2 and using the same starting materials except omitting the calcium chloride, 3,4-dichlorobutan-1-ol yields of 66–79% were achieved at conversions ranging from 64–91%.

EXAMPLE 3

Furan Ring Synthesis (Best Mode)

A 300 ml, round bottom, glass flask equipped with thermometer, magnetic stirrer, 0.152 m Vigreux still under one atmosphere of $N_2$ was charged with 10 g of 91% 3,4-dichlorobutan-1-ol (from the chlorination reaction), 70 g distilled water, 33 g calcium chloride and 2.6 g calcium hydroxide. The mixture was stirred vigorously and slowly distilled over a 3-hour period at pot temperatures of 93°–119° C. and head temperatures of 92°–100° C. The distillation was stopped when the pot temperature reached 119° C.

Most of the 3-chlorotetrahydrofuran distilled over in the first few minutes and settled to the bottom of the receiver. The remainder of the distillate was largely water containing some 3-buten-1-ol from the crude starting material and a small amount of 3-chlorotetrahydrofuran.

The total distillate, both layers, was extracted with ether and the dried ether solution was analyzed on a Carbowax ® 20 M column and found to contain 6.37 g of 3-chlorotetrahydrofuran (characterized by IR, mass spec and hydrogenolysis to THF). This corresponded to a 94.5% yield at 100% conversion of the 3,4-dichlorobutan-1-ol. Analysis of the pot contents and the distillate by gas chromatography showed the absence of 3,4-dichlorobutan-1-ol.

In the distillation from the ring closure reactor the 3-chlorotetrahydrofuran and water codistilled at 92°–93° C. Since the chlorotetrahydrofuran was more dense than water and had a very low solubility in water, it could be taken overhead and the water returned to the pot. This was accomplished by constructing a well at the take-off site in the head. As this filled with the water-3-chlorotetrahydrofuran mixture, the chlorotetrahydrofuran settled to the bottom from whence it passed into the receiver essentially pure.

Small amounts of furan, 2,3- and 2,5-dihydrofurans were formed in this ring closure reaction. A dry ice trap off the receiver was used to trap these.

EXAMPLE 4

Furan Ring Synthesis—Alcoholic Solution of Sodium Hydroxide

A 50 ml, round bottom, glass flask equipped with magnetic stirrer, 0.152 m Vigreux still, thermometer and under one atmosphere $N_2$ was charged with 2.9 g crude 3,4-dichlorobutan-1-ol, 29.6 g n-butanol and 2.05 g sodium hydroxide. The stirred flask contents were heated at 111°–119° C. for 2 hours and the product distilled at head temperature of 42°–92° C. Analysis of the distillate product mix showed it to be 84.5%, 2,5-dihydrofuran, 5.2%, 2,3-dihydrofuran and 10.3% 3-chlorotetrahydrofuran.

A similar experiment using potassium hydroxide gave the following product distribution: 90.1% 2,5-dihydrofuran, 6.4%, 2,3-dihydrofuran and 3.5% 3-chlorotetrahydrofuran.

EXAMPLE 5

Tetrahydrofuran Synthesis (Best Mode)

Crude distillate, 6.3 g (from the ring closure reaction) containing 5.0 g 3-chlorotetrahydrofuran and the remainder largely water and 3-buten-1-ol was charged into a 180 ml steel shaker tube along with 50 ml distilled water, 1.7 g calcium oxide and 0.3 g Engelhard 10% Pd on charcoal. The tube contents were chilled to −80° C., the tube was evacuated, and then pressured to 300 psi with hydrogen. The tube was then agitated at 84-0.305 m strokes/minute for ½ hour at 120° C.

The tube contents upon analysis were found to contain 3.2 g tetrahydrofuran, a small amount of residual 3-chlorotetrahydrofuran, 1-butanol but no 3-buten-1-ol. This corresponds to a 98% THF yield at 97% conversion. The THF was characterized by IR and mass spec.

In an experiment similar to that of Example 4 a 110 ml stainless steel shaker tube was charged with 3.2 g of the distillate, which was 96% 3-chlorotetrahydrofuran, 50 g distilled water, 1.1 g calcium hydroxide, and 0.2 g of 10% rhodium on carbon. The tube was heated for ½ hour at 120° C. under a hydrogen pressure of 400 psi. Subsequent analysis of the tube contents showed essentially all of the 3-chlorotetrahydrofuran to have been reacted; the yield of tetrahydrofuran was 99%.

I claim:

1. Process for the preparation of tetrahydrofuran from propylene and formaldehyde, the process comprising
   (1) reacting propylene and aqueous formaldehyde stabilized with alcohol in the presence of silica sand at a temperature of from 250°–350° C. and a pressure of from 50–800 atmospheres in the absence of oxygen at a ratio of propylene to formaldehyde of at least 1:1 to form 3-buten-1-ol;
   (2) reacting the aqueous 3-buten-1-ol with chlorine in the presence of Group IA or IIA chloride at a temperature of from 0°–50° C. and a pressure of from 5 to 50 psia in the absence of oxygen to form 3,4-dichlorobutan-1-ol;
   (3) treating 3,4-dichlorobutan-1-ol with an aqueous or alcoholic solution of Group IA or IIA base at a temperature of from 25°–200° C. and a pressure of from atmospheric to 50 psia in the absence of oxygen to form 3-chlorotetrahydrofuran or a mixture of 3-chlorotetrahydrofuran with 2,3-dihydrofuran and/or 2,5-dihydrofuran; and
   (4) hydrogenating 3-chlorotetrahydrofuran or the byproducts 2,3-dihydrofuran and 2,5-dihydrofuran in an aqueous medium with hydrogen and in the presence of a hydrogenation catalyst at a temperature of from 50°–250° C. and a pressure of 147–2000 psia in the absence of oxygen to form tetrahydrofuran.

2. The process of claim 1 wherein the chloride is calcium or sodium chloride.

3. The process of claim 1 wherein the base is sodium or calcium hydroxide and in an amount sufficient that the reaction remains at a pH in the range of about 6–8.

4. The process of claim 1 wherein a base is added to the medium in an amount sufficient to neutralize any hydrogen chloride formed.

5. The process of claim 1 wherein the catalyst is 10% palladium on charcoal or 10% rhodium on carbon.

* * * * *